United States Patent
Pamel

(10) Patent No.: US 10,925,894 B2
(45) Date of Patent: Feb. 23, 2021

(54) COMPOSITION CONTAINING CHLORINE DIOXIDE AND METHODS FOR USING SAME

(71) Applicant: Gregory J. Pamel, New York, NY (US)

(72) Inventor: Gregory J. Pamel, New York, NY (US)

(*) Notice: Subject to any disclaimer, the term of this patent is extended or adjusted under 35 U.S.C. 154(b) by 0 days.

(21) Appl. No.: 15/972,362

(22) Filed: May 7, 2018

(65) Prior Publication Data

US 2018/0318339 A1    Nov. 8, 2018

Related U.S. Application Data

(60) Provisional application No. 62/608,889, filed on Dec. 21, 2017, provisional application No. 62/502,085, filed on May 5, 2017.

(51) Int. Cl.

| A61K 47/38 | (2006.01) |
|---|---|
| A61K 9/06 | (2006.01) |
| A61K 9/127 | (2006.01) |
| A61P 27/02 | (2006.01) |
| A61K 33/00 | (2006.01) |
| A61K 9/00 | (2006.01) |
| A61K 45/06 | (2006.01) |
| A61K 33/20 | (2006.01) |
| A61P 41/00 | (2006.01) |
| A61P 31/02 | (2006.01) |
| A61K 9/51 | (2006.01) |

(52) U.S. Cl.
CPC ............ *A61K 33/00* (2013.01); *A61K 9/0014* (2013.01); *A61K 9/0048* (2013.01); *A61K 33/20* (2013.01); *A61K 45/06* (2013.01); *A61P 27/02* (2018.01); *A61P 31/02* (2018.01); *A61P 41/00* (2018.01); *A61K 9/1271* (2013.01); *A61K 9/5153* (2013.01)

(58) Field of Classification Search
CPC ........ A61K 9/0048; A61K 9/06; A61K 47/38; A61P 31/04; A61P 27/02
See application file for complete search history.

(56) References Cited

U.S. PATENT DOCUMENTS

| 3,278,447 A | 10/1966 | Mcnicholas |
|---|---|---|
| 4,177,268 A | 12/1979 | Torossian et al. |
| 5,736,165 A | 4/1998 | Ripley et al. |
| 7,767,217 B2 | 8/2010 | Samson et al. |
| 8,394,364 B2 | 3/2013 | Samson et al. |
| 8,765,724 B2 | 7/2014 | Samson et al. |
| 9,056,057 B2 | 6/2015 | Popov et al. |
| 9,308,173 B2 | 4/2016 | Liang et al. |
| 9,387,223 B2 | 7/2016 | Samson et al. |
| 2002/0035264 A1 | 3/2002 | Kararli et al. |
| 2002/0107238 A1* | 8/2002 | Bandyopadhyay .. A61K 9/0048 514/211.15 |
| 2004/0224010 A1 | 11/2004 | Hofland et al. |
| 2004/0241207 A1* | 12/2004 | Chauhan ............... A61K 9/0048 424/429 |
| 2005/0042240 A1* | 2/2005 | Utterberg ................ A61L 29/16 424/400 |
| 2005/0228046 A1* | 10/2005 | Yu .......................... A01N 33/04 514/553 |
| 2006/0263409 A1* | 11/2006 | Peyman ................ A61K 9/0051 424/427 |
| 2010/0196512 A1* | 8/2010 | Full ........................ A61K 33/20 424/661 |
| 2013/0034507 A1 | 2/2013 | Speronello et al. |
| 2013/0251783 A1 | 9/2013 | Parmentier et al. |
| 2013/0323179 A1* | 12/2013 | Popov .................. A61K 9/5031 424/9.6 |

FOREIGN PATENT DOCUMENTS

| CN | 1820607 A | | 8/2006 |
|---|---|---|---|
| KR | 20170012094 A | * | 2/2017 |
| WO | 199600275 A1 | | 1/1996 |
| WO | 1996002264 A2 | | 2/1996 |
| WO | 2008011164 A2 | | 1/2008 |

OTHER PUBLICATIONS

Li et al. Liposome coated with low molecular weight chitosan and its potential use in ocular drug delivery. Jun. 25, 2009. International Journal of Pharmaceutics. vol. 379. pp. 131-138. (Year: 2009).*
Missouri University of Science and Technology. EOR Data Group: Polymer Properties. Date Retrieved: Jun. 9, 2020. <http://web.mst.edu/~weim/EORData/polymer_evaluation.html>. (Year: 2020).*
International Search Report and Written Opinion for PCT/US2018/031318 dated Aug. 1, 2018.

* cited by examiner

*Primary Examiner* — Tracy Liu
(74) *Attorney, Agent, or Firm* — Troutman Pepper Hamilton Sanders LLP

(57) ABSTRACT

The present invention relates to a composition comprising chlorine dioxide useful in the treatment of active infections of the eye, as well as prophylaxis and treatment of such infections. The invention also relates to uses of compositions including effective amounts of chlorine dioxide in the eye to obtain benefit without detrimentally affecting the eye.

15 Claims, No Drawings

COMPOSITION CONTAINING CHLORINE DIOXIDE AND METHODS FOR USING SAME

CROSS-REFERENCE TO RELATED APPLICATIONS

This application claims the benefit of U.S. Provisional Application No. 62/502,085 and U.S. Provisional Application No. 62/608,889, each of which is incorporated herein by reference in its entirety.

GOVERNMENT INTERESTS

Not applicable

PARTIES TO A JOINT RESEARCH AGREEMENT

Not Applicable

INCORPORATION OF MATERIAL ON COMPACT DISC

Not applicable

BACKGROUND

Infectious conjunctivitis is an ophthalmic disorder characterized by inflammation of the conjunctiva secondary to invasion by a microbe. Microbes capable of causing conjunctivitis in humans include bacteria (including Mycobacteria), viruses, fungi, or amoebae. Current treatment for bacterial conjunctivitis consists of antibiotic drops. However, ocular surface bacteria are becoming increasingly resistant to available ophthalmic antibiotic eye drops. Because antibiotic drops are ineffective against viral conjunctivitis, treatment of such infections consists only of relieving symptoms or preventing secondary bacterial infection. Treatments for fungi and amoeba conjunctivitis consist of a small selection of medications that lack anti-bacterial or anti-viral activity and which, in addition, are toxic to the ocular surface.

Diagnosis of the various causative agents such as bacteria, virus, or fungus, in infectious conjunctivitis is not economically feasible because accurate diagnosis requires sophisticated laboratory culture equipment not easily integrated into the average healthcare practice. In addition, culture results for bacterial conjunctivitis are often inconclusive because the bacteria cultured are often those that are part of the normal ocular surface flora. Viral cultures are impractical because of the length of time needed for culture results to be obtained which often exceed the period of infection. Because accurate diagnosis is impractical and because there are no approved treatments for viral conjunctivitis, most conjunctivitis is presumed to be bacterial without culturing and is treated with antibiotics. Antibiotic treatment is suboptimal because it is ineffective against viral or fungal conjunctivitis and contributes to the development of bacterial resistance. Viral conjunctivitis caused by adenovirus is extremely contagious and can lead to wide spread infection in medical offices, work place environments and households.

The use of steroids is approached cautiously in the setting of ocular infection. While steroids can have the benefit of reducing the severity of the inflammation in an acute infection, they are also known to increase susceptibility to certain infections.

There is currently no ophthalmic antimicrobial drug with broad spectrum activity against all the causes of conjunctivitis, and there is currently no approved antimicrobial/steroid, or antimicrobial/non-steroidal anti-inflammatory combination drug that has shown to be effective against and to be safely used in infectious conjunctivitis that is viral or fungal in origin.

SUMMARY OF THE INVENTION

Various embodiments are directed to compositions containing chlorine dioxide useful in the treatment of active infections of at least one tissue of the eye (e.g., the conjunctiva) from bacteria (including Mycobacteria), viruses, fungi, or amoebae, as well as treatment to prevent such infections in appropriate clinical setting (e.g., corneal abrasion, postoperative prophylaxis, post-LASIK/LASEK prophylaxis). The invention also relates to uses of compositions including effective amounts of chlorine dioxide in the eye to obtain benefit without detrimentally affecting the eye.

New uses for chlorine dioxide-containing compositions in the eye have been discovered. Compositions, which include effective amounts of chlorine dioxide, have been found to be ophthalmically acceptable for in-the-eye use. The present invention is easy and straightforward to practice. For example, the invention can be practiced using techniques used in employing prior art ophthalmic antiseptics and ocular surgical irrigants. Little or no additional cost is involved in practicing the present invention relative to using conventional ophthalmic antiseptics and ocular surgical irrigants. The chlorine dioxide-containing compositions useful in the present methods can be formed from stable precursor compositions very shortly (directly) prior to use. Such precursor compositions have relatively long shelf lives, and produce chlorine dioxide-containing compositions having reliable and reproducible chlorine dioxide concentrations which are effective as ophthalmic antiseptics and ocular surgical irrigants, and are ophthalmically acceptable.

In one broad aspect of the present invention, a composition compnsmg effective amounts of chlorine dioxide are provided that is suitable for topical administration to an eye, effective for treatment and/or prophylaxis of a microorganism infection or a disorder of at least one tissue of the eye. The therapeutic amount of chlorine dioxide in the composition is from about 0.005% (w/w) to about 10% (w/w). Such compositions are particularly effective where the eye has a microbial infection, such as bacterial conjunctivitis and/or other microbial infection, since it is effective in treating, preferably reducing or even eliminating, the microbial infection. The presently useful compositions preferably have a pH in the range of about 5 to about 10, are substantially isotonic, or a combination thereof.

In another broad aspect of the present invention, methods for treating a mammalian eye are provided. These caring methods comprise administering to a mammalian eye, preferably a human eye, an effective amount of a composition, preferably in the form of an aqueous liquid medium, which includes chlorine dioxide in an amount effective as an antiseptic in the eye. The therapeutic amount of chlorine dioxide in the composition is from about 0.005% (w/w) to about 10% (w/w). Such administering is particularly effective where the eye has a microbial infection, such as bacterial conjunctivitis and/or other microbial infection, since such administering is effective in treating, preferably reducing or even eliminating, the microbial infection. The presently useful compositions preferably have a pH in the range of about 5 to about 10, are substantially isotonic, or a combination thereof.

Various embodiments are directed to compositions containing an effective amount of chlorine dioxide and a thickening agent. In such embodiments, the chlorine dioxide may be a chlorine dioxide-containing complexes selected from the group consisting of complexes of chlorine dioxide with carbonate, complexes of chlorine dioxide with bicarbonate, stabilized oxychloro complex (SOC), and combinations thereof, and in some embodiments, the chlorine dioxide may be about 0.005% (w/w) to about 10% (w/w) of the total composition.

The thickening agent of embodiments may be selected from the group consisting of lipid thickening agents, cetyl alcohol, stearyl alcohol, carnauba wax, stearic acid, locust bean gum, xanthan gum, gelatin, balsam fir, silica, bentonite, magnesium aluminum silicate, carbomers, polyvinylpyrrolidone, polyethylene glycol, carboxymethylcellulose, hydroxyethylacrylate/sodium acryloyldimethyl taurate copolymer, vp/hexadecene copolymer, and combinations thereof. In some embodiments, the thickening agent may be a cationic polysaccharide selected from the group consisting of starch, cellulose, pectin, chitin, chitosan, guar, and combinations thereof. In certain embodiments, the thickening agent may be a functionalized cationic polysaccharides selected from the group consisting of N,N,N-trimethyl chitosan (TMC), N,N,N-trimethyl-O-(2-hydroxy-3-trimethylammonium propyl)chitosan, N,N,N-trimethyl-O-carboxymethyl chitosan (TMCMC), O-carboxymethyl chitosan (CMC), Na-form CMC, H-form CMC, N-(2-hydroxy-3-trimethylammonium)propyl chitosan (HTCC), quaternary N-(benzyl)chitosan, and combinations thereof.

In some embodiments, the composition may include quaternary ammonium salts or quaternary ammonium compounds, and in such embodiments, the quaternary ammonium salts or quaternary ammonium compounds may be selected from the group consisting of benzalkonium chloride, C10-C14-alkyl(ethylbenzyl)dimethylammonium chloride, and combinations thereof. The quaternary ammonium salts or quaternary ammonium compounds may be about 0.00005% to about 0.15% (w/w) of the total composition.

In some embodiments, the composition may further contain ophthalmic astringents, ophthalmic demulcent, ophthalmic emollients, ophthalmic hypertonicity, ophthalmic vasoconstrictor, oxygen-releasing components, viscosity agents, additional active agents, anti-inflammatories, steroids, anesthetic, antimicrobial agents, vasoconstrictor, and combinations thereof. In certain embodiments, the composition may be in a form for topical delivery selected from the group consisting of cream, lotion, ointment, gel, liquid, and spray.

Further embodiments are directed to compositions containing an effective amount of chlorine dioxide and a nanoparticles or microparticles. In such embodiments, the chlorine dioxide may be a chlorine dioxide-containing complexes selected from the group consisting of complexes of chlorine dioxide with carbonate, complexes of chlorine dioxide with bicarbonate, stabilized oxychloro complex (SOC), and combinations thereof, and in some embodiments, the chlorine dioxide may be about 0.005% (w/w) to about 10% (w/w) of the total composition. In some embodiments, the chlorine dioxide may be encapsulated within the nanoparticles or microparticles, ionically associated with the nanoparticle or microparticles, or combinations thereof.

The nanoparticles or microparticles of various embodiments may be selected from the group consisting of hybrid polyamidoamine (PAMAM) dendrimer hydrogel/poly (lactic-co-glycolic acid) (PLGA) nanoparticles or microparticles (HDNP), chitosan (CS) nanopartices or microparticles, thiolated chitosan nanoparticles or microparticles, calcium phosphate (CaP) nanoparticles or microparticles, poly (lactic-co-glycolic acid) copolymer (PLGA), poly (ethyleneglycol)-block-poly(-caprolactone) nanopolymeric nanoparticles or microparticles, core/shell nanoparticles or microparticles composed of a lecithin liposome core and pluronic F 127 diacrylate (DA-PF 127), inorganically-coated retinoic acid (atRA) nanoparticles or microparticles, poly (lactic acid) (PLA) homopolymers and PEG-block-PLA copolymer nanoparticles or microparticles, PEG-block-PPG copolymers such as Pluronic, PEGylated liposome-protamine-hyaluronic acid nanoparticles or microparticles, polylactic acid/polylactic acid-polyethylene oxide (PLA/PLA-PEO) nanoparticles or microparticles, and combinations thereof. In some embodiments, the nanoparticles may have a diameter of from about 2 nanometers to about 200 nanometers.

In particular embodiments, the nanoparticles or microparticles may be selected from the group consisting of mucous penetrating particles. Such mucous penetrating particles may include a core particle comprising at least about 80 wt. % chlorine dioxide or a chlorine dioxide precursor and less than about 20 wt % a polymer constitutes, and a surface-altering agent coating surrounding the core particle. The surface-altering agent may be a triblock copolymer having a hydrophilic block-hydrophobic block-hydrophilic block configuration in which each hydrophobic block may have a molecular weight of at least about 2 kDa and hydrophilic blocks having at least about 15 wt. % of the triblock copolymer, and in some embodiments, the surface-altering agent may have a density of at least about 0.001 molecules per nanometer squared and the coated particles may have a relative velocity of greater than 0.5 in mucus.

In certain embodiments, the nanoparticles or microparticles may be liposomes. The liposomes may include phosphatidylcholine (PC) and cholesterol, lipid-conjugated hydrophilic polymers, chitosan, and combinations thereof, and in some embodiments, the liposomes may be coated in chitosan. Such liposomes may have a mean particle diameter of about 1 nanometers to about 50 nanometers.

In some embodiments, the composition may further contain ophthalmic astringents, ophthalmic demulcent, ophthalmic emollients, ophthalmic hypertonicity, ophthalmic vasoconstrictor, oxygen-releasing components, viscosity agents, additional active agents, anti-inflammatories, steroids, anesthetic, antimicrobial agents, vasoconstrictor, and combinations thereof. In certain embodiments, the composition may be in a form for topical delivery selected from the group consisting of cream, lotion, ointment, gel, liquid, and spray.

Other embodiments are directed to compositions containing an effective amount of chlorine dioxide and colloidal lipids. In such embodiments, the chlorine dioxide may be a chlorine dioxide-containing complexes selected from the group consisting of complexes of chlorine dioxide with carbonate, complexes of chlorine dioxide with bicarbonate, stabilized oxychloro complex (SOC), and combinations thereof, and in some embodiments, the chlorine dioxide may be about 0.005% (w/w) to about 10% (w/w) of the total composition. In some embodiments, the chlorine dioxide may be encapsulated within the colloidal lipids, ionically associated with the colloidal lipids, or combinations thereof.

The colloidal polar lipids may be selected from the group consisting of one or more non-ionic polyethylene glycol derivatives of castor oil and/or hydrogenated castor oil, PEG-30 castor oil, PEG-33 castor oil, PEG-36 castor oil, PEG-40 castor oil, PEG-30 hydrogenated castor oil and PEG-40 hydrogenated castor oil, an anionic purified polysaccharide, Gellan Gum, one or more buffering agents, boric acid, trimethamine, and combinations thereof. In various embodiments, the colloidal lipids may include about 0.1% to about 15% (w/v) of the total composition.

In some embodiments, the composition may further contain ophthalmic astringents, ophthalmic demulcent, ophthalmic emollients, ophthalmic hypertonicity, ophthalmic vasoconstrictor, oxygen-releasing components, viscosity agents, additional active agents, anti-inflammatories, steroids, anesthetic, antimicrobial agents, vasoconstrictor, and combinations thereof. In certain embodiments, the composition may be in a form for topical delivery selected from the group consisting of cream, lotion, ointment, gel, liquid, and spray.

These and other aspects and advantages of the present invention will become apparent hereinafter, particularly when considered in conjunction with the examples and claims.

DESCRIPTION OF THE DRAWINGS

Not applicable

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to an "amino acid" is a reference to one or more amino acids and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering," when used in conjunction with a chlorine dioxide-containing composition, can include, but is not limited to, providing a chlorine dioxide-containing composition into or onto the target tissue; providing a chlorine dioxide-containing composition systemically to a patient by, e.g., intravenous injection whereby the therapeutic reaches the target tissue. "Administering" a composition may be accomplished by injection, topical administration, or by either method in combination with other known techniques. Such combination techniques include heating, radiation and ultrasound.

The term "animal" as used herein includes, but is not limited to, humans and non-human vertebrates such as wild, domestic, and farm animals.

As used herein, the term "antimicrobial" refers to the ability of the antimicrobial composition described herein to prevent, inhibit or destroy the growth of microbes such bacteria (including Mycobacteria), viruses, fungi, or amoebae The term "kill" and like terms, refers to the ability of an antimicrobial composition to inhibit or destroy growth of a cellular (e.g., self-replicating) microbe, such as, without limitation, a bacteria or fungus, for example, by reducing a number of colony-forming units of the cellular microbe in a bacteria culture or colony, or to inhibit growth rate of a colony or culture of cells. Likewise, with reference to virus particles or virions (e.g., non-self-replicating), the term "neutralize" refers to a reduction of infectivity of a single virion and to overall infectivity (e.g., a reduction in the number of infectious units (IU) or plaque-forming units (PFU)) of a sample of virus particles). Non-limiting examples of killing of bacteria or fungi, and neutralization of virions, and methods of testing for such killing or neutralization are provided in the Examples below.

The term "inhibiting" includes the administration of a compound of the present invention to prevent the onset of the symptoms, alleviating the symptoms, reducing the symptoms, delaying or decreasing the progression of the infection and/or its symptoms, or eliminating condition or infection.

By "pharmaceutically acceptable," it is meant the carrier, diluent or excipient must be compatible with the other ingredients of the formulation and not deleterious to the recipient thereof.

As used herein, the term "ophthalmically acceptable" refers to any material or combination of materials which, in the concentrations employed, has no undue detrimental effect on the eye or the ocular tissue with which it comes in contact.

As used herein, the term "therapeutic" means an agent utilized to treat, combat, ameliorate, prevent or improve an unwanted condition or infection of a patient. In part, embodiments of the present invention are directed to the treatment of bacteria (including Mycobacteria), viruses, fungi, or amoebae infections.

A "therapeutically effective amount" or "effective amount" of a composition is a predetermined amount calculated to achieve the desired effect, i.e., to bacteria (including Mycobacteria), viruses, fungi, or amoebae. The activity contemplated by the present methods includes both medical therapeutic and/or prophylactic treatment, as appropriate. The specific dose of a chlorine dioxide containing composition administered according to this invention to obtain therapeutic and/or prophylactic effects will, of course, be determined by the particular circumstances surrounding the case, including, for example, the chlorine dioxide administered, the route of administration, and the condition being treated. The effective amount administered will be determined by the physician in the light of the relevant circumstances including the condition to be treated, the choice of chlorine dioxide to be administered, and the chosen route of administration, and therefore the above dosage ranges are not intended to limit the scope of the invention in any way. A therapeutically effective amount of chlorine dioxide in this invention is typically an amount such that when it is administered in a physiologically tolerable excipient composition, it is sufficient to achieve an effective concentration in the ocular tissue.

The terms "treat," "treated," or "treating" as used herein refers to both therapeutic treatment and prophylactic or preventative measures, wherein the object is to prevent or slow down (lessen) an undesired physiological condition or infection, or to obtain beneficial or desired clinical results. For the purposes of this invention, beneficial or desired clinical results include, but are not limited to, alleviation of symptoms; diminishment of the extent of the condition or infection; stabilization (i.e., not worsening) of the state of the condition or infection; delay in onset or slowing of the progression of the condition or infection; amelioration of the condition or infection; and remission (whether partial or total), whether detectable or undetectable, or enhancement or improvement of the condition or infection. Treatment includes eliciting a clinically significant response without excessive levels of side effects.

Generally speaking, the term "tissue" refers to any aggregation of similarly specialized cells which are united in the performance of a particular function.

It is understood, for any of the chemicals of this disclosure, that the chemicals may be in various modified forms such as acetate forms, and sodium phosphate forms, sodium salts, and the like. It is known that any of the reagents mentioned anywhere in this disclosure may be in chemically equivalent forms such as salts, hydrides, esters and other modifications of the basic chemical. For example, dexamethasone in any of the compositions and methods of the invention may be replaced with any of its derivatives, including esters and salts thereof. Examples of such derivatives include, at least, Dexamethasone-17-acetate (CAS RN: 1177-87-3), Dexamethasone Disodium Phosphate (CAS RN: 2392-39-4), Dexamethasone Valerate (CAS RN: 14899-36-6), Dexamethasone-21-isonicotinate (CAS RN: 2265-64-7), Dexamethasone Palmitate (CAS RN: 33755-46-3), Dexamethasone Propionate (CAS RN: 55541-30-5), Dexamethasone Acefurate (CAS RN: 83880-70-0), Dexamethasone-21-galactoside (CAS RN: 92901-23-0), dexamethasone 21-thiopivalate, dexamethasone 21-thiopentanoate, dexamethasone 21-thiol-2-methyl-butanoate, dexamethasone 21-thiol-3-methyl-butanoate, dexamethasone 21-thiohexanoate, dexamethasone 21-thiol-4-methyl-pentanoate, dexamethasone 21-thiol-3,3-dimethyl-butanoate, dexamethasone 21-thiol-2-ethyl-butanoate, dexamethasone 21-thiooctanoate, dexamethasone 21-thiol-2-ethyl-hexanoate, dexamethasone 21-thiononanoate, dexamethasone 21-thiodecanoate, dexamethasone 21-p-fluorothiobenzoate or a combination thereof. Dexamethasone derivatives are also described in U.S. Pat. No. 4,177,268.

Various embodiments of the invention are directed to compositions including chlorine dioxide and methods for treating diseased tissue by administering such compositions. Such compositions and methods can be used as an antiseptic that reduces viral and bacterial load at the diseased tissue with reduced adverse effects such as irritation or swelling of contacted tissue as compared to current treatments. In particular embodiments, the compositions and methods can be used to treat ophthalmic injury or disease, and in some embodiments, the compositions and methods can be used to treat conjunctivitis.

Further embodiments are directed to compositions containing chlorine dioxide formulated for extending the residence time of chlorine dioxide on the surfaces to which the composition is administered. Chlorine dioxide is a gas that is readily soluble in aqueous solutions. The chlorine dioxide in aqueous compositions encompassed by some embodiments of the invention is quickly released when the composition is applied to a surface and the aqueous solution evaporates or is absorbed by the surface. Thus, certain embodiments are directed to compositions with improve residence time for chlorine dioxide on treated surfaces. Improved residence time can be accomplished by any means known in the art. For example, in some embodiments, residence time can be improved by increasing the viscosity of the composition. In other embodiments, the chlorine dioxide may be present in nanoparticles or microparticles, and in still other embodiments, residence time can be improved by encapsulating the chlorine dioxide in liposome or combining the chlorine dioxide with colloidal polar nanolipids. Still other embodiments, are directed to wipes having the compositions disposed one a surface.

The compositions of embodiments may at least include chlorine dioxide. Chlorine dioxide may be provided as chlorine dioxide itself or as a chlorine dioxide precursor that forms chlorine dioxide after administration. For example, chlorine dioxide-containing complexes, such as complexes of chlorine dioxide with carbonate, chlorine dioxide with bicarbonate and mixtures thereof, for example stabilized oxychloro complex (SOC), are examples of chlorine dioxide precursors. The manufacture or production of certain chlorine dioxide components is described in U.S. Pat. No. 3,278,447, which is incorporated in its entirety herein by reference. As used herein, the term "chlorine dioxide" encompasses the compound chlorine dioxide, chlorine dioxide precursors, chlorine dioxide precursors in combination with an activator or promoter, and chlorine dioxide containing complexes such as SOC. Additional examples of chlorine dioxide precursors include metal chlorites, such as alkali metal and alkaline earth metal chlorites, and chlorine carbonates, borates, sulfates, phosphates, and mixtures thereof. For example, sodium chlorite is a useful chlorine dioxide precursor component. Chlorine dioxide precursors may allow chlorine dioxide and compositions containing chlorine dioxide to be shipped and stored with minimum loss of effectiveness.

The amount of chlorine dioxide or chlorine dioxide precursor contained in the compositions can be any amount effective to act as an antiseptic. For example, a therapeutically effective amount of chlorine dioxide in compositions of the invention can be about 0.005% (w/w) to about 10% (w/w), about 0.01% (w/w) to about 9.5% (w/w), about 0.02% (w/w) to about 9.0% (w/w), about 0.03% (w/w) to about 8.5% (w/w), about 0.04% (w/w) to about 8.0% (w/w), about 0.05% (w/w) to about 7.5% (w/w), about 0.06% (w/w) to about 7.0% (w/w), about 0.07% (w/w) to about 6.5% (w/w), about 0.08% (w/w) to about 6.0% (w/w), about 0.1% (w/w) to about 5.5% (w/w), about 0.25% (w/w) to about 5.0% (w/w), about 0.5% (w/w) to about 4.5% (w/w), about 1.0% (w/w) to about 4.0% (w/w), about 1.5% (w/w) to about 3.5% (w/w), about 2.0% (w/w) to about 3.0% (w/w), or any individual concentration or range encompassed by these example ranges.

In some embodiments, the composition may further include one or more quaternary ammonium cations. Quaternary ammonium cations, also known as "quats" or "QACs," are positively charged polyatomic ions of the structure $NR_4^+$, in which R is an alkyl group or an aryl group, and are permanently charged, independent of the pH of their solution. Quaternary ammonium salts or quaternary ammonium compounds are salts of quaternary ammonium cations. The composition of various embodiments can include a quaternary ammonium cation or a quaternary ammonium salt. In some embodiments, each R may, independently be $C_2$ to $C_{14}$ alkyl chain, and in particular embodiments at least one R may be a $C_5$ to $C_{10}$ aryl or at least one R may include a $C_5$ to $C_{10}$ aryl as a substituent on an $C_2$ to $C_{14}$ alkyl chain alkyl. Each $C_5$ to $C_{10}$ aryl can be substituted with one or more $C_2$ to $C_6$ alkyl chain. For example, in some embodiments, at least one R may be ethylbenzyl. In certain embodiments, the quaternary ammonium salt may be benzalkonium chloride, $C_{10}$-$C_{14}$-alkyl(ethylbenzyl)dimethylammonium chloride, and the like or combinations thereof. Combination quaternary ammonium salts can be composed of various ratios of compounds, and the quaternary ammonium of embodiments can include $1^{st}$ generation, $2^{nd}$ generation, $3^{rd}$ generation, $4^{th}$ generation, $5^{th}$ generation quaternary ammonium salts or disinfectants. The amount of quaternary ammonium salt in the compositions of embodiments can be from about 0.00005% to about 0.15% (w/w), about 0.001% to about 0.125% (w/w), about 0.001% to about 0.1% (w/w), or any concentration or range of concentrations encompassed by these example concentrations.

The viscosity of aqueous solutions containing chlorine dioxide or chlorine dioxide can be increased by any method know in the art. For example, in some embodiments, the compositions of the invention may include a thickening agent that increases the viscosity of the compositions sufficiently to improve residence time of the chlorine dioxide. Thickening agents encompassed by the invention include, but are not limited to, lipid thickening agents, such as, cetyl alcohol, stearyl alcohol, carnauba wax, stearic acid, and the like and combinations thereof. Other thickening agents include naturally derived thickening agents, such as, locust bean gum, xanthan gum, gelatin, balsam fir, and the like and combinations thereof, and mineral thickening agents such as, silica, bentonite, magnesium aluminum silicate, and the like and combinations thereof. In still other embodiments, the thickening agent may be a synthetic thickening agent such as carbomers, polyvinylpyrrolidone, polyethylene glycol, carboxymethylcellulose, hydroxyethylacrylate/sodium acryloyldimethyl taurate copolymer, vp/hexadecene copolymer, and the like and combinations thereof. In yet other embodiments, the compositions may include any combination of two or more lipid, naturally derived, mineral, and synthetic thickening agents.

In some embodiments, the formulation may include cationic polysaccharides such as, for example, starch, cellulose, pectin, chitin, chitosan, guar, and the like. Without wishing to be bound by theory, the cationic polysaccharide may increase the concentration of chlorine dioxide and residence time of the chlorine dioxide on the mucosal surface of the eye. In particular embodiments, the cationic polysaccharides may be functionalized with a positively charged moieties that increase the number of amino groups on the cationic polysaccharide or introduce of quaternary ammonium groups, resulting in chitosan derivatives with positive charges over wide pH ranges. Such "functionalized cationic polysaccharides" may be more compatible with host tissues and may be more effective antimicrobial agents. Examples of functionalized cationic polysaccharides include, but are not limited to, N,N,N-trimethyl chitosan (TMC), N,N,N-trimethyl-O-(2-hydroxy-3-trimethylammonium propyl)chitosan, N,N,N-trimethyl-O-carboxymethyl chitosan (TMCMC), O-carboxymethyl chitosan (CMC), Na-form CMC, H-form CMC, N-(2-hydroxy-3-trimethylammonium) propyl chitosan (HTCC), quaternary N-(benzyl)chitosan, and the like and combinations thereof.

In some embodiments, formulations including cationic polysaccharides and functionalized cationic polysaccharides may further include a Flavin such as, for example, riboflavin, riboflavin-5-phosphate, flavin mononucleotide, flavin adenine dinucleotide, flavin guanine nucleotide, flavin cytosine nucleotide, and flavin thymine nucleotide, and in particular embodiments, such formulations may include riboflavin. The addition of a Flavin to the formulations of such embodiments may improve penetration of the chlorine dioxide through the mucosa of the eye and into the cornea.

Nanoparticle and microparticles can be used to aid in the delivery of chlorine dioxide or chlorine dioxide precursors to the eye. The chlorine dioxide or chlorine dioxide precursor may be encapsulated within the nanoparticles or microparticles or ionically associated with the nanoparticle or microparticles to stabilize the chlorine dioxide or chlorine dioxide precursor during delivery and improve residence. For example, in some embodiments, the compositions may include lipid nanoparticles or microparticles that can encapsulate the chlorine dioxide or chlorine dioxide precursor. Such nanoparticles can be prepared by forming an emulsion of chlorine dioxide or chlorine dioxide precursor dissolved in a solvent and glycerol and poloxomer heating and cooling the emulsion and homogenizing the emulsion. In other embodiments, the compositions may include commercially relevant nanoparticles or microparticles such as, for example, hybrid polyamidoamine (PAMAM) dendrimer hydrogel/poly (lactic-co-glycolic acid) (PLGA) nanoparticles or microparticles (HDNP), chitosan (CS) nanopartices or microparticles, thiolated chitosan nanoparticles or microparticles, calcium phosphate (CaP) nanoparticles or microparticles, poly (lactic-co-glycolic acid) copolymer (PLGA), poly (ethyleneglycol)-block-poly(-caprolactone) nanopolymeric nanoparticles or microparticles, core/shell nanoparticles or microparticles composed of, for example, a lecithin liposome as the core and pluronic F 127 diacrylate (DA-PF 127), inorganically-coated retinoic acid (atRA) nanoparticles or microparticles, poly (lactic acid) (PLA) homopolymers and PEG-block-PLA copolymer nanoparticles or microparticles, PEG-block-PPG copolymers such as Pluronic®, PEGylated liposome-protamine-hyaluronic acid nanoparticles or microparticles, polylactic acid/polylactic acid-polyethylene oxide (PLA/PLA-PEO) nanoparticles or microparticles, and the like and combinations thereof. In various embodiments, the nanoparticles may have a diameter of from about 2 to about 200 nanometers, about 5 to about 50 nanometers, or about 18 to about 22 nanometers, or any range or individual value encompassed by these ranges.

In some embodiments, the chlorine dioxide or chlorine dioxide precursors may be incorporated into a nanoparticle, and in certain embodiments, the nanoparticles may be mucous penetrating particles, such as those described in U.S. Pat. No. 9,056,057, which is hereby incorporated by reference in its entirety. In particular embodiments, the mucous penetrating particles may include a core particle containing a at least about 80 wt. % chlorine dioxide or a chlorine dioxide precursor and less than about 20 wt % a polymer constitutes, and a coating including a surface-altering agent surrounding the core particle. The surface-altering agent may include a triblock copolymer having a hydrophilic block-hydrophobic block-hydrophilic block configuration in which each hydrophobic block may have a molecular weight of at least about 2 kDa and hydrophilic blocks having at least about 15 wt. % of the triblock copolymer. In such embodiments, the hydrophobic block associates with the surface of the core particle and the hydrophilic block may form a surface of the coated particle rendering the coated particle hydrophilic. The surface-altering agent may be present on the surface of the core particle at a density of at least about 0.001 molecules per nanometer squared and the coated particles may have a relative velocity of greater than 0.5 in mucus.

Further embodiments include liposomes containing chlorine dioxide or chlorine dioxide precursors. Liposomes are well known and commonly used in the pharmaceutical arts, and any type of liposome can be used in the compositions of embodiments. For example, the liposomes may be composed of phosphatidylcholine (PC) and other constituents such as cholesterol and lipid-conjugated hydrophilic polymers. In other embodiments, the liposomes may contain chitosan or may be coated in chitosan (i.e., chitosomes), which may further improve the residence time of the chlorine dioxide or chlorine dioxide precursor.

In particular embodiments, the compositions may include colloidal lipids. Such compositions may include colloidal polar lipids formed from one or more non-ionic polyethylene glycol derivatives of castor oil and/or hydrogenated castor oil such as, for example, PEG-30 castor oil, PEG-33 castor oil, PEG-36 castor oil, PEG-40 castor oil, PEG-30 hydrogenated castor oil and PEG-40 hydrogenated castor oil, an anionic purified polysaccharide such as Gellan Gum, one or more buffering agents such as, for example, boric acid, trimethamine, and, in some embodiments, one or more aqueous lubricants and one or more colloidal aqueous lubricants. The colloidal lipids may form particles about 1 nanometers to about 50 nanometers or about 6 nanometers to about 22 nanometers, and the compositions may include about 0.1 to about 15% w/v colloidal lipids. Without wishing to be bound by theory, such compositions may coat the eye, limiting evaporation and contact of the chlorine dioxide or chlorine dioxide precursor with atmospheric oxygen, thereby improving residence time of the chlorine dioxide or chlorine dioxide precursor.

The compositions of various embodiments including thickening agents, nanoparticles, liposomes, or colloidal lipids may increase the contact time of the composition on the eye. Chlorine dioxide or chlorine dioxide precursor in an aqueous buffer system may exhibit a relatively short residence time on the eye, for example, less than 1 minute. Increasing the viscosity, encapsulating the chlorine dioxide or chlorine dioxide precursor in a nanoparticle or liposome, or combining chlorine dioxide or a chlorine dioxide precursor with a colloidal lipid may effectively increase the residence time of the active agent on the eye by up to about 2 to about 10 times that of a simple solution. Increasing residence time may allow for improved activity and/or reduce the requirement for readministration. Thus, a solution that is administered 4 to 8 times per day, may be administered twice daily and achieve the same level of activity.

The compositions of embodiments can include various additional components know and useful in the ophthalmic arts. For example, the compositions may include an ophthalmic astringent that helps clear mucous from the surface of the eye by precipitating protein. Such ophthalmic astringents include, for example, zinc sulfate and the like. In some embodiments, the compositions may include an ophthalmic demulcent that protects and lubricates mucous membranes such as, for example, cellulose derivatives, carboxymethcellulose sodium, hydroxyethyl cellulose, hydroxypropyl methylcellulose, methylcellulose, dextran 70, gelatin, liquid polyols, glycerin, polyethylene glycol 300, polyethylene glycol 400, polysorbate 80, polyvinyl alcohol, povidone, and the like and combinations thereof. In some embodiments, the compositions may include ophthalmic emollients, which protects or softens tissues surrounding the eye and to prevent drying and cracking such as, for example, lanolin, anhydrous lanolin, lanolin, oleaginous ingredients, light mineral oil, mineral oil, paraffin, petrolatum, white ointment, white petrolatum, white wax, yellow wax, and the like and combinations thereof. In some embodiments, the compositions may include an ophthalmic hypertonicity agent such as sodium chloride and the like. In some embodiments, the compositions may include an ophthalmic vasoconstrictor such as, ephedrine hydrochloride, naphazoline hydrochloride, phenylephrine hydrochloride, tetrahydrazoline hydrochloride, and the like and combinations thereof. The compositions of various embodiments can include any combination of the above components. For example, in certain embodiments, the compositions may include an astringent and a vasoconstrictor; any 2-3 demulcents; a demulcent and a vasoconstrictor; an astringent, a vasoconstrictor, and a demulcent; and the like.

The compositions of embodiments may further include various solvents and other components that buffer or stabilize the formulation, improve shelf-life, and activate the composition upon delivery. The solvent can be any solvent that does not produce substantial detrimental effect on effected tissue such as the eye or ocular tissue being cared for or irrigated. In certain embodiments, the solvent may be aqueous-based, such as saline, conventional saline solution, or conventional buffered saline solution. The solvent may have a pH in the range of about 5 to about 10, about 5 to about 8, or any individual value or range encompassed by these example ranges. In certain embodiments, the solvent may have ophthalmically acceptable tonicity levels, for example, of at least about 200 mOsmol/kg, or about 200 mOsmol/kg to about 400 mOsmol/kg.

The amount of buffer component employed is preferably sufficient to provide the precursor-containing liquid medium with the desired pH. Under mildly acidic conditions, in particular at a pH of less than about 6 and especially in the pH range of about 3 to about 5, the production of chlorine dioxide is affected from the chlorine dioxide precursors. As such, during chlorine dioxide generation using acid activation, a liquid medium may have a pH of about 6 or less, in particular in the pH range of about 3 to about 5. Any suitable acidic component may be employed as the activator. The primary criteria for such acidic component is that it has the ability to increase the acidity of the liquid medium containing chlorine dioxide precursor sufficiently to effect formation of chlorine dioxide from such chlorine dioxide precursor, and preferably sufficiently to effect formation of antiseptic amounts or disinfecting amounts of chlorine dioxide from the presently useful chlorine dioxide precursors. Such acidic components should also have no substantial detrimental effect on the tissue being cared for. Examples of acidic components include mineral acids, salts of such mineral acids, carboxylic acids, salts of such carboxylic acids and mixtures thereof. The mineral acids include, for example, citric acid, sulfuric acid, hydrogen halides, phosphoric acid and the like. The carboxylic acids include both mono- and poly-, e.g., di-, tri- and the like, carboxylic acids, and preferably include 1 to about 10 carbon atoms per molecule. One or more non-hydrocarbonaceous groups, e.g., hydroxy groups, halide groups and the like, may be appended to the carboxylic acid. If any acid salt is employed, it is preferred that the salt be an alkali or alkaline earth metal salt, more preferably an alkali metal salt. A particularly useful group of acidic components is selected from alkali metal hydrogen phosphates, citric acid, lactic acid, tartaric acid and mixtures thereof.

Effective amounts of buffer components, tonicity adjusting components, or the combination thereof may be included to provide that such compositions have the desired pH values, tonicities, or the combination thereof. Buffer components, tonicity adjusting components, or the combination thereof useful in other ophthalmic-related compositions may be employed in the presently useful compositions. In addition, one or more other components, such as those known to be useful in ophthalmic-related compositions, may be included in the presently useful compositions in amounts effective to provide such compositions with one or more desired properties. For example, the form of the presently useful compositions may be obtained, maintained, or the combination thereof using one or more of such other components, as fillers, emollients, surfactants and the like. While the precise regimen is left to the discretion of the clinician, it is recommended that the resulting solution be topically applied by placing one drop in each eye 1 to 24 times daily. For example, the solution may be applied 1, 2, 4, 6, 8, 12, 18 or 24 times a day.

Oxygen-releasing components useful as activator components in the present invention include both inorganic and organic peroxy compounds. For example, in some embodiments, the oxygen-releasing components such as water soluble inorganic salts such as, for example, the sodium, potassium, calcium, magnesium, lithium and ammonium salts of oxygen-releasing sulfur compounds, such as, for example, the perthiosulfates ($S_2O_5\bullet$) the persulfates ($OS_5$-2), the peroxysulfates, such as the peroxymonogulfates ($HSO_5\bullet$) and the peroxydisulfates($S_2O_8$-2), and combinations thereof, can be used in the combination with chlorine dioxide precursors. In particular embodiments, the oxygen-releasing component can be potassium peroxymonosulfate ($KHSO_5$) or a triple salt form of potassium peroxymonosulfate containing potassium peroxymonosulfate ($KHSO_5$), potassium hydrogen sulfate ($KHSO_4$), and potassium sulfate ($K_2SO_4$), and the like and combinations thereof. This composition is an acidic, water soluble, oxygen releasing powder that is odorless, white, granular, stable and free flowing. Other alkali metal, e.g., sodium, and ammonium salts are also useful. Among useful organic peroxy compounds are the aliphatic and aromatic percarboxylic acids. Examples of the aliphatic peracids include peracetic acid, perpropionic acid, up to perlauric acid. The preferred peracids are aromatic such as perbenzoic acid and nuclear substituted perbenzoic acids, especially those having melting points above 50° C. Especially preferred is p-methoxyperbenzoic acid. The amount of oxygen-releasing component during the chlorine dioxide production may be about 0.01 mole or less to about 1 mole or more per mole of potential chlorine dioxide present as chlorine dioxide precursor in the medium. Particularly useful results are achieved using oxygen-releasing component in the range of about 0.01 mole to about 0.1 mole per mole of potential chlorine dioxide present as chlorine dioxide precursor in the medium.

Any suitable activator component may be employed to affect the generation of chlorine dioxide from the presently useful chlorine dioxide precursor components. Examples include, acidic materials to increase the acidity of the medium, transition metal components, oxygen-releasing components, organic acid anhydrides, chlorine dioxide reducing components and the like. In addition, an electrical current can be passed through a chlorine dioxide precursor-containing liquid medium to effect formation of chlorine dioxide Such compositions may be formulated for topical administration, such as topical administration to the eye. The compositions of embodiments can be formulated as percent by weight solutions in water, saline, or other medical solution.

The compositions of embodiments can further include various additional active agents, such as, anti-inflammatories, steroids, anesthetic, antimicrobial agents, and the like, and combinations thereof. In certain embodiments, the chlorine dioxide or chlorine dioxide precursor containing composition may improve the effectiveness of such active agents. For example, the chlorine dioxide or chlorine dioxide precursor may act as an enhancer for the active agent reducing the necessary concentration to achieve therapeutically effective activity.

In some embodiments, the composition may further include an anti-inflammatory. Numerous anti-inflammatory agents are available in the prior art and any such agents can be used in the compositions of embodiments. For example, suitable anti-inflammatories may include ketotifen fumarate, diclofenac sodium, flurbiprofen sodium, ketorlac tromethamine, suprofen, celecoxib, naproxen, rofecoxib, or a derivative or combination thereof. Ketorolac (also called ketorlac, or ketorolac tromethamine) is a non-steroidal anti-inflammatory drug (NSAID) in the family of propionic acids.

In certain embodiments, the composition may further include a steroid. Numerous steroids are available in the prior art and any such agents can be used in the compositions of embodiments. For example, suitable steroids include, but are not limited to, dexamethasone, dexamethasone alcohol, dexamethasone sodium phosphate, fluromethalone acetate, fluromethalone alcohol, lotoprendol etabonate, medrysone, prednisolone, prednisone, prednisolone acetate, prednisolone sodium phosphate, rimexolone, hydrocortisone, hydrocortisone acetate, lodoxamide tromethamine, methylprednisolone, or a derivative or combination thereof.

In further embodiments, the composition may further include an anesthetic. Numerous anesthetics are available in the prior art and any such agents can be used in the compositions of embodiments. For example, suitable anesthetics include proparacaine, lidocaine, tetracaine, and derivatives or combination thereof.

In some embodiments, the composition may further include an antimicrobial agent. Numerous antimicrobial agents are available in the prior art and any such agents can be used in the compositions of embodiments. For example, suitable antimicrobial agents include, but are not limited to, benzalkonium chloride, thimerosal, chlorobutanol, methyl paraben, propyl paraben, phenylethyl alcohol, EDTA, sorbic acid, Onamer M (polyquatemium-1), sodium chloride, tyloxapol, sodium sulfate, hydroxyethylcellulose, silver sulfadiazine, colloidal silver, hydrogen peroxide, polyhexamethylene biguanide, myristamidopropyl dimethylamine, and other agents known to those skilled in the art, or a combination thereof. Typically, such preservatives are employed at a level from about 0.001% (w/w) to about 1.0% (w/w).

In some embodiments, the composition may include a vasoconstrictor. Numerous vasoconstrictors are available in the prior art and any such agent can be used in the compositions of embodiments. For example, suitable vasoconstrictors include the following: about 0.01% (w/w) to about 1% (w/w) ephedrine hydrochloride, about 0.001% (w/w) to about 1% (w/w) naphazoline hydrochloride, about 0.001% (w/w) to about 0.5% (w/w) phenylephrine hydrochloride, about 0.001% (w/w) to about 0.5% (w/w) tetrahydrazoline hydrochloride, and the like, or a derivative or combination thereof.

The compositions may be in any suitable form for topical delivery such as a cream, lotion, ointment, gel, liquid, spray and the like, and are preferably administered directly to injured tissue. Such compositions may be in the form of a solution, suspension or emulsion. In various embodiments, the composition may further include various additives such as, for example, co-solvents, viscolsity agents, astringents, demulcents, emollients, hypertonicity agents, preservatives, and combinations thereof.

In particular embodiments, the composition may contain a co-solvent. The solubility of the components of the compositions discussed above may be enhanced by a surfactant or other appropriate co-solvent in the composition. Such co-solvents include, for example, various surfactants, polysorbate 20, 60, and 80, polyoxyethylene/polyoxypropylene surfactants, cyclodextrin, tyloxapol, poloxamer 237 and the like, or combinations thereof. Typically, such co-solvents are employed at a level of from about 0.01% to about 2% by weight.

In some embodiments, the compositions may contain a viscosity agent used to increase viscosity of the composition. Viscosity increased above that of simple aqueous solutions may be desirable to increase absorption of the active compound, to decrease variability in dispensing the composition, to decrease physical separation of components of a suspension or emulsion of the compositions or otherwise improve the composition. Such viscosity agents include, for examples polyvinyl alcohol, polyvinyl pyrrolidone, methyl cellulose, hydroxy propyl methylcellulose, hydroxyethyl cellulose, carboxymethyl cellulose, hydroxy propyl cellulose, and the like, or combinations thereof. Such agents are typically employed at a level of from about 0.01% to about 2% by weight.

In some embodiments, the compositions may include an astringent. Suitable ophthalmic astringents include, for example, zinc sulfate, and the like, or a derivative or combination thereof. Typically, such agents are employed at a level from about 0.005% to about 2% by weight.

In further embodiments, the compositions may further include a demulcent. Suitable demulcents include, for example, about 0.05% (w/w) to about 5% (w/w) carboxymethcellulose sodium, about 0.05% (w/w) to about 5% (w/w) hydroxyethyl cellulose, about 0.05% (w/w) to about 5% (w/w) hydroxypropyl methylcellulose, about 0.05% (w/w) to about 5% (w/w) methylcellulose, about 0.005% (w/w) to about 1.0% (w/w) Dextran 70, about 0.005% (w/w) to about 1.0% (w/w) Gelatin, about 0.005% (w/w) to about 5.0% (w/w) Glycerin, about 0.005% (w/w) to about 5.0% (w/w) polyethylene glycol, about 0.005% (w/w) to about 1.0% (w/w) polysorbate, about 0.005% (w/w) to about 10% (w/w) polyvinyl alcohol, about 0.005% (w/w) to about 5.0% (w/w) povidone, or a derivative or combinations thereof.

In another embodiment, the composition may further include emollients. Suitable emollients include, for example, about 0.1% (w/w) to about 20% (w/w) anhydrous lanolin, about 0.1% (w/w) to about 20% (w/w) lanolin, about 0.005% (w/w) to about 50% (w/w) mineral oil, about 0.005% (w/w) to about 10% (w/w) paraffin, about 0.005% (w/w) to about 100% (w/w) petrolatum, about 0.005% (w/w) to about 100% (w/w) white ointment, about 0.005% (w/w) to about 100% (w/w) white petrolatum, about 0.005% (w/w) to about 10% (w/w) white wax, about 0.005% (w/w) to about 10% (w/w) yellow wax, or derivatives or combinations thereof.

In further embodiments, the composition may include a hypertonicity agent. Suitable hypertonicity agents include the following: about 0.1% (w/w) to about 10% (w/w) sodium chloride, or derivatives or combinations thereof.

In some embodiments, the composition may include a preservative. Suitable preservatives include, for example, benzalkonium chloride, polyquad, sodium perborate, stabilized oxychloro complex, ocupure, polyhexamethylene biguanide, chlorobutanol, edetate disodium, polyaminopropyl biguanide, polyquaternium, or derivatives or combinations thereof.

In some embodiments, the composition may further include sorbitol, hyaluronic acid, sodium hyaluronate, carnitine, erythritol, hydroxypropyl guar, polyacrylic acid, tyloxapol, tromethamine, or derivatives or combinations thereof. In some embodiments, the composition may further include hyaluronan, sulfobetaine, poloxamine, boric acid, sodium borate, edetate disodium, sodium chloride, hydroxyalkylphosphonate, propylene glycol, or derivatives or combinations thereof.

In some embodiments, the composition may further include hydrogen peroxide, lactic acid, halogen salts, salts of heavy metals, chlorhexidine, dodecyl-methyl-polyoxyethyl-ammonium propionate, chlorides of ammonium, ammonium propylamide, lauryl sulphate, dodecyl sulphate, alkyl succinic salts, ethyl alcohol, isopropyl alcohol, chlorhexidine, non-chlorinated quaternary ammonium salts, chlorinated quaternary ammonium salts, dodecyl-methyl-polyoxy-ethyl-ammonium propionate, iodine, benzyl dimethyl ammonium chloride, sodium tetraborate decahydrate, terric GN9, dipropylene glycol methyl ether, alkali metals, alkaline earth metals, hypochlorite, sodium hydroxide, or derivatives or combinations thereof.

The compositions of various embodiments can include chlorine dioxide, a solvent and any combination of additional components discussed above. For example, certain embodiments include a composition that is a solution of about 5.0 w/w % to about 0.005 w/w % chlorine dioxide and saline (about 0.9 w/v % sodium chloride in water). In other embodiments, the composition may contain about 5.0 w/w % to about 0.005 w/w % chlorine dioxide, saline, and one or more preservatives, demulcents, emollients, or combinations thereof. In still other embodiments, the composition may include about 5.0 w/w % to about 0.005 w/w % chlorine dioxide, saline, and one or more steroid, astringent, or combinations thereof. In yet other embodiments, the composition may include about 5.0 w/w % to about 0.005 w/w % chlorine dioxide, saline, and one or more antimicrobial agent. In additional embodiments, the compositions may include about 5.0 w/w % to about 0.005 w/w % chlorine dioxide, saline, one or more steroid, astringent, or combinations thereof, and one or more antimicrobial agents. In particular embodiments, the compositions may include about 5.0 w/w % to about 0.005 w/w % chlorine dioxide, saline, and colloidal silver. In such embodiments, one or more preservatives, demulcents, emollients, or combinations thereof may additionally be included in the compositions as needed. For example, in some embodiments, the compositions described above may be used as a solution for cleaning, disinfecting, or combination thereof of contact lens. In other embodiments, the compositions described above may be used as a cleaning, disinfecting, or combination thereof of surgical instruments in surgical procedures and presurgical and postsurgical antiseptic used at the time of surgery. Although not required, the container for the compositions of the invention may be clear, translucent, and opaque and may contain other properties or combination of properties such as being glass lined, tamper proof, packaged in single or few dose aliquots, and a combination thereof.

The composition may be provided in a container in liquid or cream form, whereby it may be applied to the skin by a user by hand.

Certain embodiments are directed to a transplant media containing chlorine dioxide or a chlorine dioxide precursor, which can be included in addition to antibiotics or in the absence of antibiotics, and in particular embodiments, the transplant medium may be corneal transplant media. Current transplant storage media do not contain anti-fungal agents and are therefore susceptible to fungal contamination. Chlorine dioxide has been shown to be an effective anti-fungal agent as well as a broad-spectrum antibiotic. As such, the addition chlorine dioxide to commercially available transplant media or replacing antibiotic components of these transplant media with chlorine dioxide or chlorine dioxide precursor may provide both antibiotic activity and anti-fungal activity to the transplant media.

For example, various embodiments include commercially available transplant medium such as Optisol, Dexsol, McCarey-Kaufman medium, K-Sol, Corneal Storage Medium (CSM), Minimal Essential Medium (MEM), H-Sol, Physiological Salne Solution, Eagle's Media, cell culture media, tissue culture media, cell storage media, tissue storage media, and the like containing 0.005% (w/w) to about 10% (w/w) chlorine dioxide or chlorine dioxide precursor or any of the concentrations disclosed above. In particular embodiments, the transplant media may contain minimum essential media (MEMS), HEPES buffer, HEPES without L-glutamine, TC-199 and the like and combinations thereof decomplemented calf serum or decomplemented fetal calf serum; L-glutamine; about 1 w/w % to about 10 w/w % chondroitin sulfate; about 0.05 w/w % to about 5 w/w % dextran; one or more antibiotics such as penicillin, garamycin, amphotericin B, and about containing 0.01% (w/w) to about 10% (w/w) chlorine dioxide or chlorine dioxide precursor. In other embodiments, the media may include minimum essential media (MEMS), HEPES buffer, HEPES without L-glutamine, TC-199 and the like and combinations thereof; decomplemented calf serum or decomplemented fetal calf serum; L-glutamine; about 1 w/w % to about 10 w/w % chondroitin sulfate; about 0.05 w/w % to about 5 w/w % dextran; and about containing 0.01% (w/w) to about 10% (w/w) chlorine dioxide or chlorine dioxide precursor. In such embodiments, the media may contain no antibiotics or anti-fungal agent other than chlorine dioxide or chlorine dioxide precursor. As such, various embodiments are directed to antimicrobial and antifungal transplant media.

Particular embodiments are directed to wipes in which the composition may be embedded or soaked into a plurality of sheets or wipes, allowing the composition to be applied to the skin by wiping the sheet, wipe, or other device. The composition may be soaked into a sheet or a wipe and provided to the user in this form. The user then removes the soaked wipe from a suitable air-tight package and applies it directly to the skin. Thus, a system or package may include a plurality of wipes in a resealable package, where each wipe has been soaked in or otherwise contains a cleansing composition of the present invention. The wipes are desirably disposable and include degradable components, rendering them environmentally friendly and sound.

Additional embodiments are directed to methods for using the compositions described above. For example, embodiments include methods for reducing viral and bacterial load by contacting tissue with a composition including chlorine dioxide.

In some embodiments, such methods may include contacting an eye with a composition including chlorine dioxide or a chlorine dioxide precursor. In some embodiments, such methods may include contacting an eye with a composition including chlorine dioxide or a chlorine dioxide precursor and an active agent such as those discussed above. In other embodiments, such methods may include contacting the eye with a composition including chlorine dioxide or a chlorine dioxide precursor and contacting an eye with a composition containing an active agent. In such embodiments, contacting an eye with the composition including chlorine dioxide or a chlorine dioxide precursor can be carried out before or after the step of contacting the eye with a composition including an active agent. The composition including chlorine dioxide or a chlorine dioxide precursor can be formulated to improve residence time as discussed above, for example, formulated with increased viscosity, formulated with nanoparticles or microparticles, formulated in liposomes, formulated with colloidal nanolipids, or such compositions can be administered using wipes soaked in any such composition described above.

For example, the compositions embodied by the description above can be formulated as a solution for ophthalmic delivery and the methods may include administering a drop of the solution to an eye, using any of the many types of eye drop dispensers on the market. Administering can include periodic or repeated applications of the chlorine dioxide containing composition to the eye. Such periodic applications to eyes, which are susceptible to, but do not have, microbial infections, may ameliorate or prevent microbial infections in the eyes. In certain embodiments, the dosage for one eye may be about one drop of solution, which can include about 10 µl (microliters) to about 200 µl, about 20 µl to about 120 µl, or about 50 µl to about 80 µl of solution, or any values in between. For example, dispensers such as pipettors can dispense fluid drops from at least 1 µl to 300 µl, and any value in between.

The methods described above can be used for caring for mammalian, in particular human, eyes and may be effective, in the concentration employed, to kill microorganisms such as, for example, bacteria, viruses, fungi, protozoa, and the like that comes in contact with the composition. Specifically, with regard to ophthalmic methods, the compositions, including chlorine dioxide described above, may be effective to reduce or eliminate an existing microbial, for example, bacterial, viral, fungal, or protozoa infection in an eye with which it comes in contact and/or to prevent microbial infections in an eye with which it comes in contact. In certain embodiments, such methods may be effective for treating bacterial or viral conjunctivitis.

The present methods preferably further include producing the chlorine dioxide-containing compositions from precursor compositions including chlorine dioxide precursor components. This producing step may occur directly prior to the administering steps of the present methods or the composition may be produced days, months, or years before the administering step. In this manner, the presently useful compositions can be produced when needed, and have a consistent and well controlled potency (effectiveness) or chemical make-up so as to be both effective as an ophthalmic antiseptic or an ophthalmic surgical irrigant and ophthalmically acceptable to avoid detrimentally affecting the eye being cared for or the ocular area undergoing surgery.

In some embodiments, the compositions described above may be used as an irrigant in ocular surgical procedures and presurgical and postsurgical antiseptic used at the time of surgery.

The invention claimed is:

1. An ophthalmic composition in the form of a gel, comprising an effective amount of chlorine dioxide, about 0.05% (w/w) to about 5% (w/w) methylcellulose, and a liquid medium comprising an aqueous solution.

2. The composition of claim 1, wherein the chlorine dioxide is encapsulated within nanoparticles or microparticles, ionically bonded to nanoparticle or microparticles, or combinations thereof.

3. The composition of claim 1, wherein the chlorine dioxide is chlorine dioxide containing complexes selected from the group consisting of complexes of chlorine dioxide with carbonate, complexes of chlorine dioxide with bicarbonate, stabilized oxychloro complex (SOC), and combinations thereof.

4. The composition of claim 1, wherein the chlorine dioxide comprises about 0.005% (w/w) to about 10% (w/w) of the total composition.

5. The composition of claim 2, wherein the nanoparticles or microparticles are selected from the group consisting of hybrid polyamidoamine (PAMAM) dendrimer hydrogel/poly (lactic-co-glycolic acid) (PLGA) nanoparticles or microparticles (HDNP); chitosan (CS) nanoparticles or microparticles; thiolated chitosan nanoparticles or microparticles; calcium phosphate (CaP) nanoparticles or microparticles; poly (lactic-co-glycolic acid) copolymer (PLGA) nanoparticles or microparticles; poly (ethyl eneglycol)-block-poly(caprolactone) nanoparticles or microparticles; core/shell nanoparticles or microparticles composed of a lecithin liposome core; PEG-block-PPG diacrylate copolymer (DA-PF 127) nanoparticles and microparticles; inorganically-coated retinoic acid (atRA) nanoparticles or microparticles; poly (lactic acid) (PLA) homopolymers and PEG-block-PLA copolymer nanoparticles or microparticles; PEG-block-PPG copolymer nanoparticles and microparticles; PEGylated liposome-protamine-hyaluronic acid nanoparticles or microparticles; polylactic acid/polylactic acid-polyethylene oxide (PLA/PLA-PEO) nanoparticles or microparticles; and combinations thereof.

6. The composition of claim 1, wherein the composition comprises nanoparticles having a diameter of from about 2 nanometers to about 200 nanometers.

7. The composition of claim 1, wherein the composition comprises nanoparticles or microparticles selected from the group consisting of mucous penetrating particles.

8. The composition of claim 7, wherein the mucous penetrating particles include a core particle comprising at least about 80 wt. % chlorine dioxide or chlorine dioxide precursor and less than about 20 wt. % polymer, and a surface-altering agent coating surrounding the core particle.

9. The composition of claim 8, wherein the surface-altering agent comprises a triblock copolymer having a hydrophilic block-hydrophobic block-hydrophilic block configuration in which each hydrophobic block have a molecular weight of at least about 2 kDa.

10. The composition of claim 8, wherein the surface-altering agent has a density of at least about 0.001 molecules per nanometer squared and the coated particles have a relative velocity of greater than 0.5 in mucus.

11. The composition of claim 1, wherein the composition comprises liposomes.

12. The composition of claim 11, wherein the liposomes comprise phosphatidylcholine (PC) and cholesterol, lipid-conjugated hydrophilic polymers, chitosan, or combinations thereof.

13. The composition of claim 11, wherein the liposomes are coated in chitosan.

14. The composition of claim 11, wherein the liposomes have a mean particle diameter of about 1 nanometers to about 50 nanometers.

15. The composition of claim 1, further comprising ophthalmic astringents, ophthalmic demulcent, ophthalmic emollients, ophthalmic hypertonicity, ophthalmic vasoconstrictor, oxygen-releasing components, viscosity agents, additional active agents, anti-inflammatories, steroids, anesthetic, antimicrobial agents, vasoconstrictor, or combinations thereof.

* * * * *